United States Patent [19]

Bang et al.

[11] Patent Number: 5,248,696
[45] Date of Patent: Sep. 28, 1993

[54] COMPOSITION AND METHOD FOR TREATING TUMORS

[75] Inventors: Soon D. Bang, Clifton, Va.; Stuart K. Johnson, Briarwood, N.Y.; John C. S. Park, Oakland, N.J.

[73] Assignee: World Research Institute for Science and Technology, Inc., Long Island, N.Y.

[21] Appl. No.: 687,719

[22] Filed: Apr. 18, 1991

[51] Int. Cl.$^5$ .............................................. A61K 31/19
[52] U.S. Cl. ..................................................... 514/557
[58] Field of Search ........................................ 514/557

[56] References Cited

U.S. PATENT DOCUMENTS

| | | | |
|---|---|---|---|
| 2,177,530 | 10/1939 | Littmann | 260/666 |
| 2,364,454 | 12/1944 | Lieber et al. | 252/52 |
| 2,376,382 | 5/1945 | Price et al. | 260/97 |
| 2,758,970 | 8/1956 | Saukaitis et al. | 252/8.55 |
| 2,761,790 | 9/1956 | Eckhardt et al. | 106/218 |
| 2,767,162 | 10/1956 | Picha | 260/103 |
| 2,772,260 | 11/1956 | Yeager | 260/102 |
| 2,776,238 | 1/1957 | Kelm | 167/30 |
| 2,813,895 | 10/1957 | Hasbrouck | 260/501 |
| 3,374,217 | 3/1968 | Summers, Jr. et al. | 260/109 |
| 4,117,159 | 10/1977 | Murai et al. | 424/309 |
| 4,193,931 | 3/1980 | Loeliger | 260/410.9 |
| 4,312,631 | 1/1982 | Cuntze et al. | 8/583 |
| 4,786,496 | 11/1988 | Watanabe et al. | 514/560 |

OTHER PUBLICATIONS

Chemical Abstracts 101:78846d (1984).
CA 76: 141080g (1972).
Ref. Zh. Khim, 1971, Abstr. No. 8Zh623.
Pharmaceutical Chemical Journal, vol. 6, No. 10 (1972), pp. 647–650.
Bull. Environ. Contam. Toxicol. 18: 42–47 (1977).
J. Allergy Clin. Immunol. Mar. 1989: 610–618.
Journal of Traditional Chinese Medicine 5(2): 115–118 (1985).
The Merck Index, Tenth Edition, Monograph No. 1.
J. Am. Chem. Soc. 77: 2823–2825 (1955).
Fieser and Fieser "Natural Products Related to Phenanthene," Third Edition (1949), pp. 40–45.
Ind. Eng. Chem. Prod. Res. Develop., vol. 9, No. 3: 304–310 (1970).
Synthetic Communications 6(8): 559–561 (1976).
Ind. Eng. Chem. Prod. Res. Develop., vol. 12, No. 3: 241–246 (1973).
J. Org. Chem. 34: 1940–1942 (1968).
J. Org. Chem. 32: 3758–3762 (1967).
J. Org. Chem. 32: 3763–3766 (1967).
J. Chem. Eng. Data, vol. 16, No. 13: 299–301 (1971).
J. Org. Chem., vol. 36, No. 25: 3899–3906 (1971).
J. Org. Chem., vol. 36, No. 22: 3271–3276 (1971).
Acta Chemica Scandinavica B 33: 76–78 (1979).
Helvetica Chemica Acta—vol. 65, Fasc. 5—No. 127: 1343–1350 (1982).
Helvetica Chemica Acta—vol. 65, Fasc. 3—No. 66: 661–670 (1982).
Xenobiotica, vol. 16, No. 8: 753–767 (1986).
J. Lipid Res., 5: 600–608 (1964).
J. Immunol. Meth., 68: 167–175 (1984).

*Primary Examiner*—Jerome D. Goldberg
*Attorney, Agent, or Firm*—Dilworth & Barrese

[57] ABSTRACT

A composition and method for treating tumors with resin acids and derivatives thereof are provided.

10 Claims, 4 Drawing Sheets

COMPOSITION AND METHOD FOR TREATING TUMORS

BACKGROUND OF THE INVENTION

The present invention is directed to a composition and method for treating tumors. More specifically, the present invention is directed to the treatment of tumors involving administration of certain rosin extracts including abietic acid, other resin acids, and their derivatives.

Traditionally, tumors have been treated by surgery, radiation, chemotherapy, or a combination of any of these treatments. Recognition that malignant cells tend to spread systemically through the body has resulted in recent emphasis on chemotherapeutic treatment to attack such tumor cells. However, chemotherapy administration is, at the very least, extremely debilitating, while toxicity continues to be a difficult problem. Additionally, difficulties have been encountered with selectivity of action by chemotherapeutic agents against certain malignant cells, while problems of providing a suitable delivery mechanism of such drugs have also been experienced. Accordingly, the search continues for improved anti-cancer treatments which minimize toxicity, improve selectivity of action (i.e. attack only malignant tumors), and enhance delivery of active agents to the situs of such malignant tumors and cells.

For example, U.S. Pat. No. 4,193,931 discloses 7-(substituted indanyl or naphthyl)-3-methyl-octa-2,4,6-triene derivatives which are useful as anti-tumor agents. U.S. Pat. No. 4,786,496 relates to an immunopotentiator having anti-tumor activity which is derived from marine chlorella. Ref. Zh. Khim 1971, Abstr. No. 8Zh623 (CA76: 141080g (1972)) states that certain specific alkylating derivatives of abietic acid, dehydroabietic acid and 6-hydroxyabietic acid exhibited antitumor activity against certain sarcomas. At the same time, other alkylating derivatives of these acids were found to be very toxic, while still other alkylating derivatives were documented as exhibiting no or very weak anti-tumor activity. *Pharmaceutical Chemistry Journal* Volume 6, No. 10 (1972), pages 647–650 also documents these specific test results.

SUMMARY OF THE INVENTION

It is an object of the present invention to provide a composition and method for the treatment of tumors.

It is a particular object of the invention to provide a tumor-treating composition of reduced toxicity.

It is another object of the present invention to provide for improved selectivity in treating tumors.

These and other objects are achieved by the tumor-treating composition of the present invention which comprises a tumor-treating effective amount of at least one compound of the general formula (I):

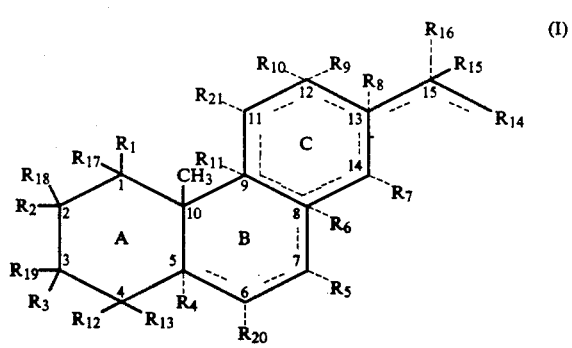

wherein
$R_1$ is H or OH,
$R_2$ is H, OH or OCOOH,
$R_3$ is H, $OCH_3$ or $CH(COOCH_3)_2$,
$R_4$, when present, is H or $OCH_3$,
$R_5$, when present, is H, =O, $CH_2OH$ or $CH_2OCOCH_3$,
$R_6$, when present, is H, OH, CHO or $CHS_2$,
$R_7$, when present, is H, =O, Cl, OH, $OCH_3$, COOH, OCOOH, $CH_2OH$ or $CH_2OCOCH_3$,
$R_8$, when present, is H, $CH_3$ or OH,
$R_9$, when present, is H or $CH_3$,
$R_{10}$, when present, is H, Cl, $CH_3$, $CH_2Cl$, $CH_2CN$, $CH_2OH$, $COOCH_3$, $CH_2COOH$, $CH_2CH_2NH_2$, $CH_2OCOCH_3$, $CH_2CH_2NCO$, $CH_2COOCH_3$, $CH_2CH_2NHCONHC_6H_5$, $CH_2O(CH_2CCH_3OH)_xH$ where x is a positive integer, $CH_2CH_2NHCONHC_6H_{11}$, $CH_2OCO(CH_2)_4COOC_2H_4OH$ or $CH_2CH_2NH_2 \cdot HOOCC_6H_3(NO_2)_2$,
$R_{11}$, when present, is H or OH,
$R_{12}$ is H, $CH_3$ or $COOCH_3$,
$R_{13}$ is CN, $CH_3$, COCl, COOH, $CONH_2$, $COCH_3$, $CH_2OH$, $CH_2NH_2$, $COOCH_3$, $CH_2NCO$, $CH_2OCOOH$, $CH_2OCOCH_3$, $CH_2O(CHCHO)_xH$ where x is a positive integer, $CH_2NHCONHC_6H_5$, $CH_2NHCONHC_6H_{11}$, $CH_2O$ $(CH_2CCH_3HO)_xH$ where x is a positive integer, $CH_2NH_2 \cdot HOOCC_6H_3(NO_2)_2$ or $CH_2OCO(CH_2)_4COOC_2H_4OH$,
$R_{14}$ is H, $CH_3$, $CH_2$, COOH, $CH_2OH$ or $COOCH_3$,
$R_{15}$ is H, OH, OCOOH,
$R_{16}$, when present, is H, $CH_3$ or $CH_2OH$,
$R_{17}$ is H or OH,
$R_{18}$ H, OH or OCOOH,
$R_{19}$ is H, $OCH_3$ or $CH(COOCH_3)_2$,
$R_{20}$, when present, is H, =O, $CH_2OH$ or $CH_2OCOCH_3$, and
$R_{21}$, when present, is H or $CH_3$,
and the pharmaceutically acceptable salts thereof together with a pharmaceutically acceptable carrier therefor.

In formula (I) supra, the dashed lines (-----) denote optional presence of substituents and optional double bonds, i.e., unsaturation. For example, unsaturation of bonds can be present at any of the positions on the "C" ring in formula (I) supra, e.g., position nos. 8, 9, 11, 12, 13 and 14. If, e.g., unsaturation is observed at the no. 12 position on ring "C" in formula (I) supra, namely a double bond is present either from position no. 12 to position no. 11 or from position no. 12 to position no. 13, then one of groups $R_9$ and $R_{10}$ will not be present. However, there is no requirement that unsaturation must be present at any of the positions on rings B or C or along the chain extending from the no. 13 position on ring "C".

The present invention is also directed to a method for treating a tumor which comprises administering a tumor-treating effective amount of a compound of the above formula (I) to a mammal possessing a tumor.

BRIEF DESCRIPTION OF THE DRAWINGS

The present invention will be explained in greater detail with reference to the accompanying drawings in which.

DESCRIPTION OF THE PREFERRED EMBODIMENTS

Figure 1:
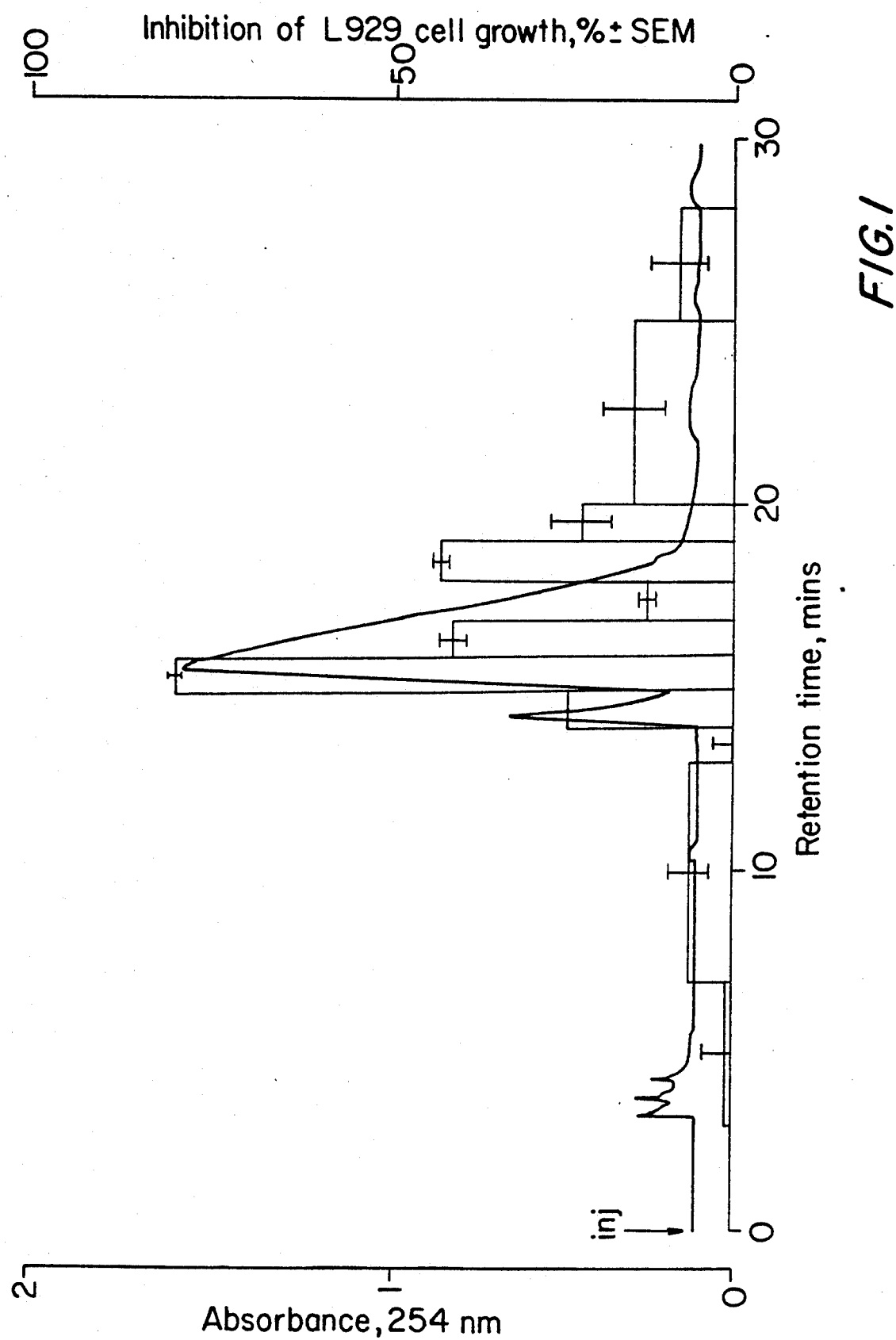
FIG. 1 is a graph comparing retention time of different rosin fractions, including those of the present invention, eluted from a normal phase chromatographic column, with ultraviolet light absorbance and inhibition of tumor cell growth.

The active tumor-treating agents of this invention are all rosin extracts including abietic acid, other resin acids, and derivatives thereof. Resin acids including abietic acid are isolated from rosin which is obtained primarily from coniferous trees. Rosin is a complex mixture of compounds with abietic acid being a principal constituent thereof. Rosin is easily modified to yield a number of different products, including levopimaric and abietic acids. In particular, abietic acid is prepared by isomerization of rosin as presented in Harris, Sanderson, *Org. Syn. Coll.* Vol. IV, 1 (1963). For example, abietic acid can be prepared by heating rosin alone or with other acids (Merck Index, Tenth Edition, Entry #1).

More specifically, the limpid oleoresin exuding from incisions cut in the bark of living pine trees is separated by steam distillation into a steam volatile fraction, a small amount of gum turpentine, and a nonvolatile residue which, upon cooling, forms a yellow/brown glassy substance which is known as rosin. Rosin is primarily composed of diterpene acids of the formula $C_{19}H_{29}COOH$ in various stages of isomerization which are known as resin acids (Fieser and Fieser, "Natural Products Related to Phenanthrene", Third Edition, 1949, Reinhold Publishing Corporation (New York)). Other extractable acids from pine are predominantly fatty acids. Virtually all pine resin acids belong to one of four basic ring structures, abietane, pimarane, isopimarane and labdane. Some of these resin acids undergo isomerization and disproportionation upon exposure to inorganic acid and/or heat. For example, levopimaric acid which is also a principal resin acid component from coniferous trees is transformed in early stages of heating to roughly equal amounts of palustric and abietic acids, followed by further isomerization of palustric acid into abietic acid, as noted in *J. Am. Chem. Soc.* 77:2823–2825.

The abietic acid, which is the end product of acid isomerization of pine tree extract, is partially isomerized to neoabietic acid upon further heating, while the abietic acid suffers disproportionation at higher temperature to yield mixtures of dehydroabietic acid, dihydroabietic acid, and tetrahydroabietic acid (Fieser and Fieser, supra). Preferably, abietic acid can be purified from crude resin by High Performance Liquid Chromatography (HPLC) which involves pumping the resin through a column packed with substrate, whereby the resin fractionates into various constituents, including the abietic acid, as the resin flows along the column. The resulting abietic acid fraction is then eluted at the appropriate rate from the column and preferably passed through a second column packed with different substrate to further purify the acid, followed by elution once again.

The purified abietic acid fraction can be esterified by the procedure described in *J. Lipid Res.*, 5: 600–608 to form an abietic acid derivative in formula (I) supra where $R_{13}$ is $COOCH_3$. In this procedure, the abietic acid fraction and respective alcohol are dissolved in a suitable organic solvent such as hexane, and then heated in a water bath, preferably from about 95° to about 100° C. for about 20 to about 60 minutes to generate the compound of formula (I) supra where $R_{13}$ is $COOCH_3$. Water is then added to form two separate layers, namely an aqueous layer and an organic layer, with the organic layer being separated and evaporated to dryness. The resulting acid ester is then purified by the HPLC procedure described supra.

Three main classes of resin acids, derived from the abietane, pimarane and isopimarane skeletons, were isolated from rosin. Formulas (II), (III) and (IV) illustrate these classes, shown as the fully saturated resin acid.

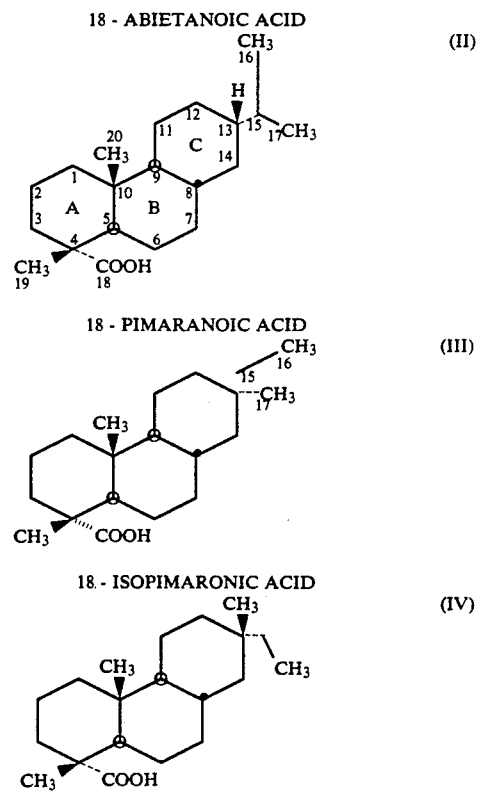

In formulas (II), (III) and (IV) supra, the dashed lines (-----) denote positioning of the substituent groups below the plane and the flared lines denote positioning of the substituent groups above the plane. By the same token, the hollow or open circles on the ring structure denote positioning of the respective juncture below the plane, while the filled in circle denotes positioning of the respective juncture above the plane, in formulas (II), (III) and (IV). In other words, all conceivable isomers of abietic, isopimaric, and pimaric acids are encompassed by the resin acids of the present invention. By the same token, all isomers of any derivatives of these resin acids (where the R groups represent any of the other substituents noted in formula (I) supra) are encompassed by the present invention.

More particularly, the derivatives of abietic, isopimaric and pimaric acids can be prepared by procedures conventionally available in the field. For example, an abietic acid derivative of formula (I) supra where $R_{10}$ is $CH_2OH$, $CH_2O(CH_2CCH_3OH)_xH$, $CH_2OCO(CH_2)_4COOC_2H_4OH$, $R_{13}$ is $COOH$, $CH_2OH$, $CH_2O(CH_2CCH_3OH)_xH$, $CH_2OCO(CH_2)_4COOC_2H_4OH$, and unsaturated bonding can be present between the no. 7 and no. 8 positions, the no. 8 and no. 14 positions, and the no. 14 and no. 13 positions on the ring structure, e.g., 12-hydroxymethyldihydroabietic acid and the dihydro isomers thereof, can be prepared by the procedure outlined in Ind. Eng. Chem. Prod. Res. Develop. Vol. 9, No. 3 (1970): 304–310. An abietic acid derivative of formula (I) supra where $R_5$ is H or =O, $R_{12}$ is $COOCH_3$, and $R_{13}$ is $COOH$ or $COOCH_3$, and unsaturation is observed around the "C" ring, i.e. the "C" ring is aromatic, can be prepared by the procedure outlined in Synthetic Communications 6 (8): 559–561 (1976). An abietic acid derivative of formula (I) supra where $R_{13}$ is $COOH$ or $COOCH_3$, $R_5$ is H or $CH_2OH$, $R_7$ is H or $CH_2OH$, $R_{10}$ is H or $CH_2OH$, and there are double bonds between the nos. 7 and 8 positions and between the nos. 13 and 14 positions on the ring structure, can be prepared according to the procedure described in Ind. Eng. Chem. Prod. Res. Develop. Vol. 12, No. 3 (1973): 241–245.

An abietic acid derivative of formula (I) supra where $R_{13}$ is $COOH$ or $COOCH_3$, $R_{10}$ is $CH_2OH$, and in which double bonds are present between the nos. 7 and 8 positions, and optionally between the nos. 9 and 11 positions on the ring structure, can be prepared according to the procedure described in J. Org.. Chem. 34 (1968): 1940–1942, while synthesis of this compound is also described in J. Org. Chem. 32 (1967): 3758–3762; this latter reference also describes synthesis of an abietic acid derivative of formula (I) supra where $R_{13}$ is $COOH$ or $COOCH_3$, $R_{10}$ is $CH_2OH$, $CH_2OCOCH_3$ or $CH_3$, and $R_{11}$ is H or OH.

Preparation of abietic acid derivatives of formula (I) above where $R_{13}$ is $COOH$, $COOCH_3$ or $CH_2OCOCH_3$, $R_5$ is $CH_2OH$ or $CH_2OCOCH_3$, $R_{10}$ is $CH_2OCOCH_3$, $CH_2OH$, $CH_3$ or H, and a double bond is present between the nos. 7 and 8 positions, and/or between the nos. 8 and 14 positions, and/or between the nos. 13 and 14 positions on the ring structure, is described in J. Org. Chem. 32: 3763–3767 (1967). Synthesis of various dinitrile, diamine and diisocyanate derivatives of hydroxymethylabietanoic acid, namely the compound of formula (I) supra where $R_{13}$ is $COOH$, $COOCH_3$, $COCl$, $CONH_2$, $CN$, $CH_2NH_2$, $CH_2HCONHC_6H_5$, $CH_2NH_2 \cdot HO_2CC_6H_3(NO_2)_2$, $CH_2NCO$ or $CH_2NHCONHC_6H_{11}$, and $R_{10}$ is $CH_2OH$, $CH_2OCOCH_3$, $CH_2Cl$, $CH_2CN$, $CH_2COOH$, $CH_2COOCH_3$, $CH_2CH_2NH_2$, $CH_2CH_2NHCONHC_6H_5$, $CH_2CH_2NH_2 \cdot HOOCC_6H_3(NO_2)_2$, $CH_2CH_2NCO$, or $CH_2CH_2NHCONHC_6H_{11}$ is set forth in J. Chem. Eng. Data Vol. 16, No. 13 (1971): 299–301.

J. Org. Chem. Vol. 36, No. 25 (1971): 3899–3906 describes synthesis of abietic acid derivatives of formula (I) above where $R_{13}$ is $COOH$ or $COOCH_3$, $R_{10}$ is H, $COOH$ or $COOCH_3$, $R_8$, when present, is OH, and $R_7$ is =O, $OCH_3$ or OH. Additionally, J. Org. Chem. Vol. 36, No. 22 (1971): 3271–3276 discloses the synthesis of abietic derivatives of formula (I) supra where $R_{13}$ is $COOH$ and double bonds are present between the nos. 8 and 14 positions on ring "C" and also between the no. 13 position on ring "C" and the no. 15 carbon atom. Lower life forms such as microbes can be utilized to synthesize several of the resin acid derivatives of formula (I) supra, as disclosed in Acta Chemica Scandinavica B 33 (1979): 76–78, Helvetica Chemica Acta—Vol. 65, Fasc. 5 (1982)—Nr-127: 1343–1350, and Helvetica Chimica Acta—Vol. 65, Fasc. 3 (1982)—Nr. 66: 661–670. Mammals can also be utilized to synthesize several of the resin acid derivatives of formula (I) supra, as noted in Xenobiotica Vol. 16, No. 8 (1986): 753–767. Therefore, the synthesis of all the resin acids and derivatives thereof listed in formula (I) supra is clearly well-known.

Preferably, the composition of the present invention comprises the compound of formula (I) supra wherein $R_1$ is H, $R_2$ is H, $R_3$ is H, $R_4$ is H, $R_5$ when present is H, $R_6$ when present is H, $R_7$ when present is H, $R_8$ when present is H or $CH_3$, $R_9$ when present, is H, $R_{10}$ when present is H, $R_{11}$ when present is H, $R_{12}$ is $CH_3$, $R_{13}$ is $CH_3$ or $COOH$, $R_{14}$ is H, $CH_2$ or $CH_3$, $R_{15}$ is H or $CH_3$, $R_{16}$ when present is H or $CH_3$, $R_{17}$ is H, $R_{18}$ is H, $R_{19}$ is H, $R_{20}$ when present is H, and $R_{21}$ when present is H.

More specifically, the composition of the present invention preferably comprises at least one compound selected from the group consisting of 18-abietanoic acid; 13 beta-abietan-18-oic acid; 8 alpha, 13 beta-abietan-18-oic acid; 9 beta, 13 beta-abietan-18-oic acid; 7-abieten-18-oic acid; 13 beta-abiet-7-en-18-oic acid; 8-abieten-18-oic acid; 13 beta-abiet-8-en-18-oic acid; 8(14)-abieten-18-oic acid; 13 beta-abiet-8(14)-en-18-oic acid; 13-abieten-18-oic acid; 8 alpha-abiet-13-en-18-oic acid; 13(15)-abieten-18-oic acid; 7, 13-abietadien-18-oic acid; 8, 13-abietadien-18-oic acid; 8, 12-abietadien-18-oic acid; 8,13(15)-abietadien-18-oic acid; 8(14), 13(15)-abietadien-18-oic acid; 13 beta-abieta-7,9(11)-dien-18-oic acid; 8(14), 12-abietadien-18-oic acid; 8,11,13-abietatrien-18-oic acid; 6,8,11,13-abietatetraen-18-oic acid; 5 beta-abieta-8,11,13-trien-18-oic acid; 18-isopimaranoic acid; 8 alpha-isopimaran-18-oic acid; 7-isopimaren-18-oic acid; 8-isopimaren-18-oic acid; 8(14)-isopimaren-18-oic acid; 7,15-isopimaradien-18-oic acid; 8,15-isopimaradien-18-oic acid; 8(14),15-isopimaradien-18-oic acid; 18-pimaranoic acid; 8 alpha-pimaran-18-oic acid; 8-pimaren-18-oic acid; 8(14)-pimaren-18-oic acid; 8,15-pimaradien-18-oic acid; and 8(14),15-pimaradien-18-oic acid.

More preferably, in the compound of formula (I) supra, $R_6$ is not present, i.e., there is an unsaturated double bond extending from the no. 8 position on the fused ring structure, while $R_{13}$ is $COOH$ and $R_{14}$ is $CH_2$ or $CH_3$. In other words, the composition of the present invention includes at least one of the following compounds: 8,15-isopimaradien-18-oic acid; 8,15-pimaradien-18-oic acid; 7,15-isopimaradien-18-oic acid; 13 beta-abieta 7,9(11)-dien-18-oic acid; 5 beta-abieta-8,11,13-trien-18-oic acid; 8,12-abietadien-18-oic acid; 7,13- abietadien-18-oic acid, and 8(14), 13(15)-abietadien-18-oic acid.

Non-toxic, pharmaceutically acceptable acid addition salts of these resin acids and derivatives thereof can be prepared by conventional reactions with equivalent amounts of organic or inorganic solutions. Exemplary acid addition salts include hydrochloric, hydrobromic, sulfuric, benzenesulfonic, acetic acid, fumaric acid, oxalic acid, malic acid, citric acid, potassium hydroxide, and sodium hydroxide salts of the abietic derivatives herein.

These resin acids and derivatives thereof and/or the pharmaceutically acceptable salts thereof are combined with a pharmaceutically acceptable carrier for administration to an individual. For example, the derivatives can be combined with a suitable liquid carrier for parenteral administration, including water, alcohol, propylene glycol and to provide a suitable composition for application. Such compositions can be injected intravenously, intraperitoneally, intramuscularly or applied topically. The compositions can also be formulated for oral administration in liquid or solid form. Suitable carriers for this administration route include water, alcohol, oil.

A particular aspect of this invention comprises a composition containing the resin acid or derivative and/or salt in an "effective amount", i.e., an amount sufficient to bring about the desired anti-tumor or tumor treating effect. In this regard, the invention is also directed to a method of treating tumors which comprises administering an effective amount of said abietic acid derivative.

A preferred concentration of the resin acid or derivative thereof and/or salt is from about 0.01 to about 0.50 mg/mg of carrier, more preferably from about 0.02 to about 0.30 mg/mg carrier and most preferably from about 0.05 to about 0.20 mg/mg carrier. A daily dosage of administration of the resin acid or derivative thereof and/or salt is preferably from about 100 to about 800 mg/kg individual, more preferably from about 200 to about 700 mg/kg individual and most preferably from about 300 to about 600 mg/kg individual.

The compositions of the present invention containing one or more of the resin acids or derivatives thereof herein are effective against a variety of tumors including L929 cells (ATCC #CCL 1: NCTC Clone 929, clone of strain L., connective tissue); S 180 cells (ATCC #TIB 66; Sarcoma 180, sarcoma swiss webster), Ehrlich-Lettre Carcinoma cells (ATCC #CCL 77: Strain E, Ehrlich-Lettre Ascites) and against other tumor cells including, non-small cell lung cancer, small cell lung cancer, colon cancer, CNS cancer, melanoma, ovarian cancer, and renal cancer cells. At the same time, these resin acids and derivatives thereof are selective against only tumor cells, i.e., they do not tend to attack normal cells. In this regard, the resin acids and derivatives are less toxic, e.g., than the compounds disclosed in *Ref. Zh. Khim* and *Pharmaceutical Chemistry Journal* cited supra.

The present invention will be described in greater detail by way of the following examples:

EXAMPLE 1

Step (A)

Obtaining Major and Minor Active Fractions of Rosin 4 mg. of rosin was chromatographed using a silica HPLC column of 25 cm. length and 10 mm. internal diameter containing silica particles of about 5 microns in size. Fractions were collected, evaporated to dryness, and redissolved in 20 μl of methanol, with the methanol extracts of the individual fractions each being mixed with 2 ml of culture medium containing L929 tumor cells. The ability of each fraction to inhibit tumor cell growth was measured according to an assay technique based on the one designed by Flick and Gifford in *J. Immunol. Meth.* 68 (1984): 167–175. FIG. 1 is a graph of the ability of these various rosin fractions to inhibit growth of L929 tumor cells, also illustrating ultraviolet (UV) absorbance of each fraction.

More specifically, FIG. 1 indicates two main peaks of biological activity among the fractions against the L929 tumor cells. The fraction of largest activity (termed "major active fraction"), exhibits maximum UV absorbance at 254 nm. The fraction of next highest activity (termed "minor active fraction"), eluted from the HPLC column approximately three minutes after the major active fraction (the abscissa of the graph in FIG. 1 denotes the elution time from the HPLC column).

STEP (B)

Purifying Major Active Fraction of Rosin Obtained in Step (A)

The major active fraction of rosin obtained in Step (A) was then chromatographed by HPLC using an ODS1 reverse phase column of 25 cm. length and 4.6 mm. internal diameter containing carbon-coated silica particles. Fractions eluting through the reverse phase column at different times were collected, evaporated to dryness, and re-dissolved in 20 μl of methanol, with the methanol extracts of the individual fractions each being mixed with 2 ml of culture medium containing L929 tumor cells. The inhibiting activity of each fraction was measured as in Step (A) above, with the results being presented in FIG. 2.

Figure 2:
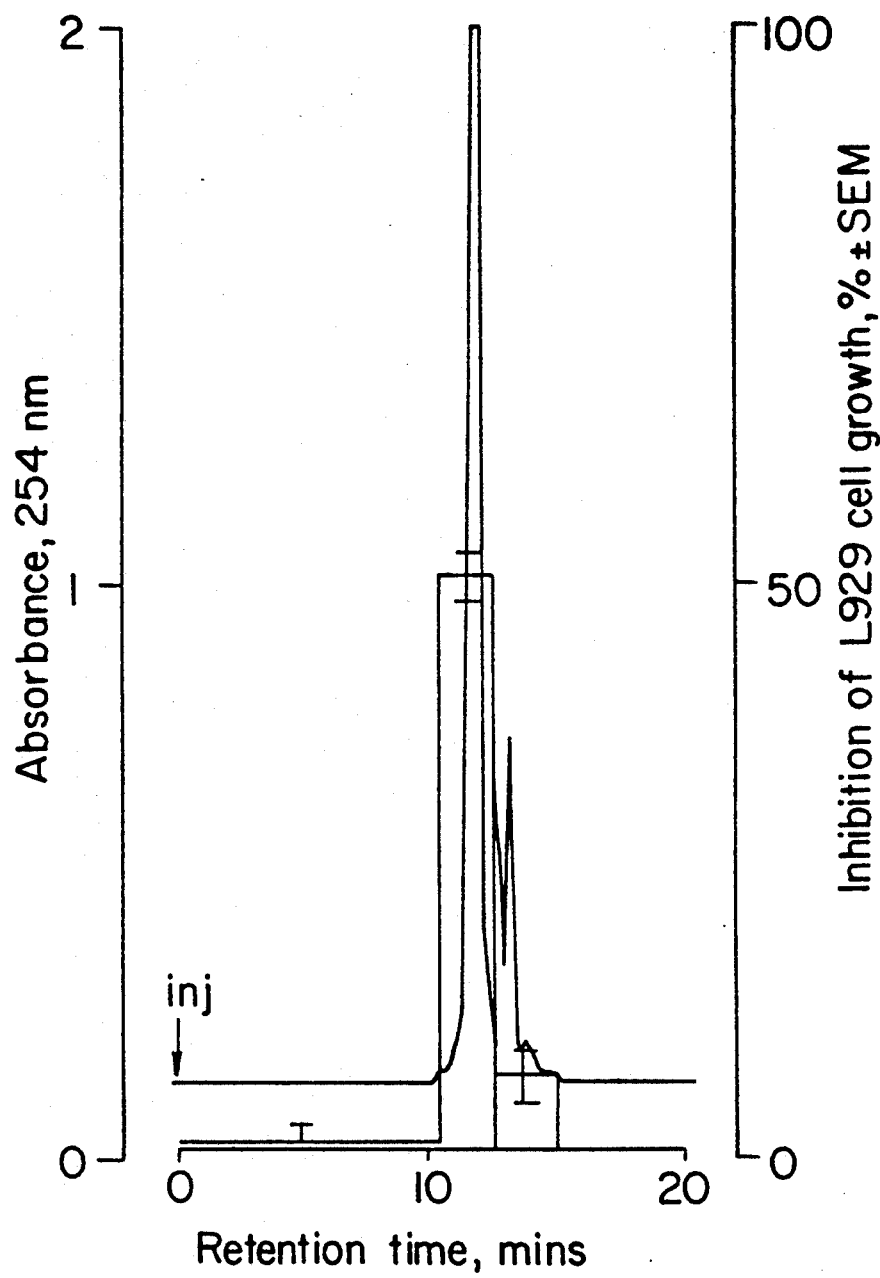
FIG. 2 is a graph comparing retention time of a purified resin acid fraction from FIG. 1 eluted from a reverse phase chromatographic column, with ultraviolet light absorbance and inhibition of tumor cell growth.

FIG. 2 indicates one peak of biological activity, coincident with maximum absorbance at 254 nm. The fraction exhibiting this peak was designated the "purified major active fraction".

STEP (C)

Methyl Esterification of Purified Major Active Fraction from Step (B)

The purified major active fraction from Step (B) was added to 350 microliters of methanol in a tube followed by the addition of 0.3 ml hexane and 0.35 ml BF$_3$ reagent, the tube thereafter being sealed under nitrogen. The sealed tube was then incubated in boiling water for 40 minutes and cooled. 2 ml. hexane and 1 ml. water were added to the opened tube, the tube then being shaken for 2 minutes, then allowed to stand to create phase separation into organic and aqueous layers. The organic (hexane) layer was removed and evaporated to dryness, and then re-dissolved in 200 μl of a solvent mixture of 1–5% dioxane and 1–5% methanol in hexane and subjected to HPLC in a silica column of 25 cm. length and 10 mm. internal diameter containing silica particles of about 5 microns in size. The solvent system was introduced into the silica column at a constant flow rate of 3 ml/min.

At the same time, the eluted fractions were subjected to ultraviolet spectroscopy to analyze the composition thereof. It was found that the fraction composed of resin acid methyl esters eluted almost at the void volume within the silica column, in other words almost immediately. The non-esterified resin acids eluted at a slower rate.

The isolated resin acid methyl ester fraction was collected, evaporated to dryness, re-dissolved in alcohol, and then subjected to gas chromatography/mass spectroscopy, with the analysis establishing the presence of methyl esters of a fraction constituted by the following resin acids in the following proportions in Table 1 below for the major active fraction (methyl esterification enabled identification of resin acids constituting the original fraction):

TABLE 1

| Resin Acid In Purified Major Active Fraction | % Of Total Resin Acids In Major Active Fraction |
| --- | --- |
| 8,15-isopimaradien-18-oate | 5.2 |
| 8,15-pimaradien-18-oate | 3.2 |
| 7,15-isopimaradien-18-oate | 9.2 |
| 13β-abieta-7,9(11)-dien-18-oate) 5β-abieta-8,11,13-trien-18-oate) | 2.2 |
| 8,12-abietadien-18-oate | 1.1 |
| 7,13-abietadien-18-oate | 78.6 |
| 8(14),13(15)-abietadien-18-oate | 0.5 |

EXAMPLE 2

A technical grade abietic acid fraction was purified by normal phase HPLC, reverse phase HPLC (ODS1) and methyl esterified in accordance with the procedure outlined in steps (A), (B) and (C) respectively of Example 1. Table 2 below lists the constituents and percentages in the purified abietic acid fraction that were identified by the methyl esterification:

TABLE 2

| Resin Acid In Purified Abeitic Acid Fraction | % Of Total Resin Acids In Abietic Acid Fraction |
| --- | --- |
| 8,15-isopimaradien-18-oate | 3.5 |
| 7,15-isopimaradien-18-oate | 8.9 |
| 13β-abieta-7,9(11)-dien-18-oate) | 9.7 |
| 5β-abieta-8,11,13-trien-18-oate) 8,12-abietadien-18-oate | 2.5 |
| 7,13-abietadien-18-oate | 72.5 |
| 8(14),13(15)-abietadien-18-oate | 1.8 |
| unknown | 1.1 |

EXAMPLE 3

In accordance with the procedure outlined in Canc. Res. 47: 3707–3711, female CD1 mice (obtained from Charles River Laboratories) were inoculated intraperitoneally with $10^6$ S 180 cells in 100 microliters of phosphate buffered saline (PBS). Controls received PBS only. Both tumor and control mice were divided into three groups of ten mice per group. Rosin and technical grade abietic acid were each dissolved in ethanol at a concentration of 200 mg/ml which was diluted with 10% newborn calf serum in PBS to a ratio of 1:20 to form respective suspensions. Untreated groups (both tumor and control mice) were inoculated intraperitoneally with 1 ml of vehicle alone while technical grade abietic acid treated groups (both tumor and control) were intraperitoneally inoculated with 1 ml (10 mg) of the rosin suspension and the technical grade abietic acid treated groups (both tumor and control) were intraperitoneally inoculated with 1 ml (10 mg) of the technical grade abietic acid suspension, the doses being administered immediately, and thereafter on the third, sixth and ninth days. Data from animals which expired within two hours of any inoculation (at zero, three, six and nine days) were discarded. The survival rates of the various treated and untreated groups is plotted against time in FIG. 3 with mice surviving longer than ninety days being deemed cured of the original intraperitoneal tumor burden. FIG. 4 records animal weight (growth rate) over time of the tumor-free group, with n denoting the number of mice in each treated group in FIGS. 3 and 4.

Technical grade abietic acid includes the various constituents of Table 2 supra as principal ingredients, in addition to other minor amounts of associated resin acids.

Figure 3:
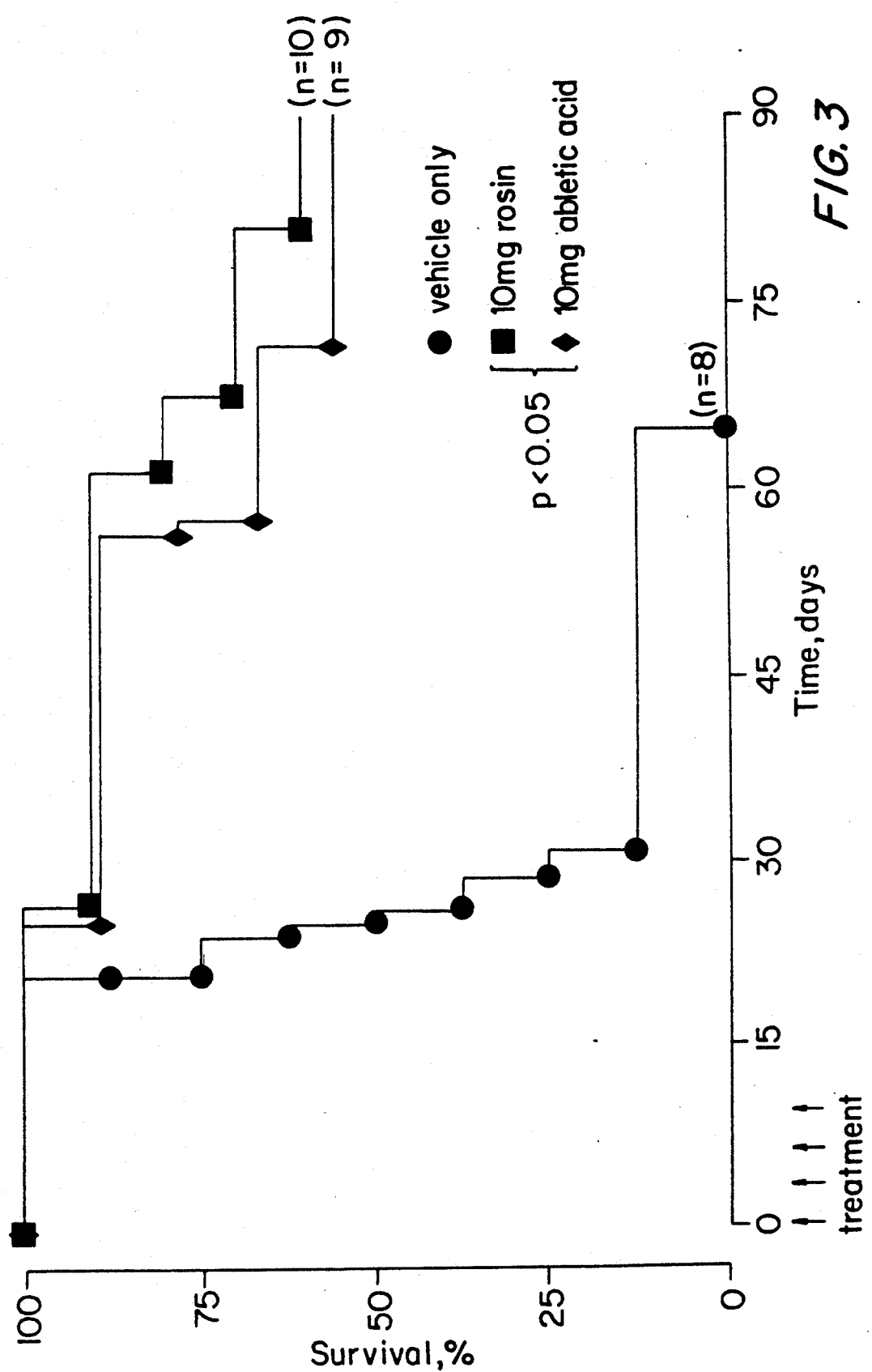
FIG. 3 is a graph comparing survival times of mice treated with different compositions, including those of the present invention.
Figure 4:
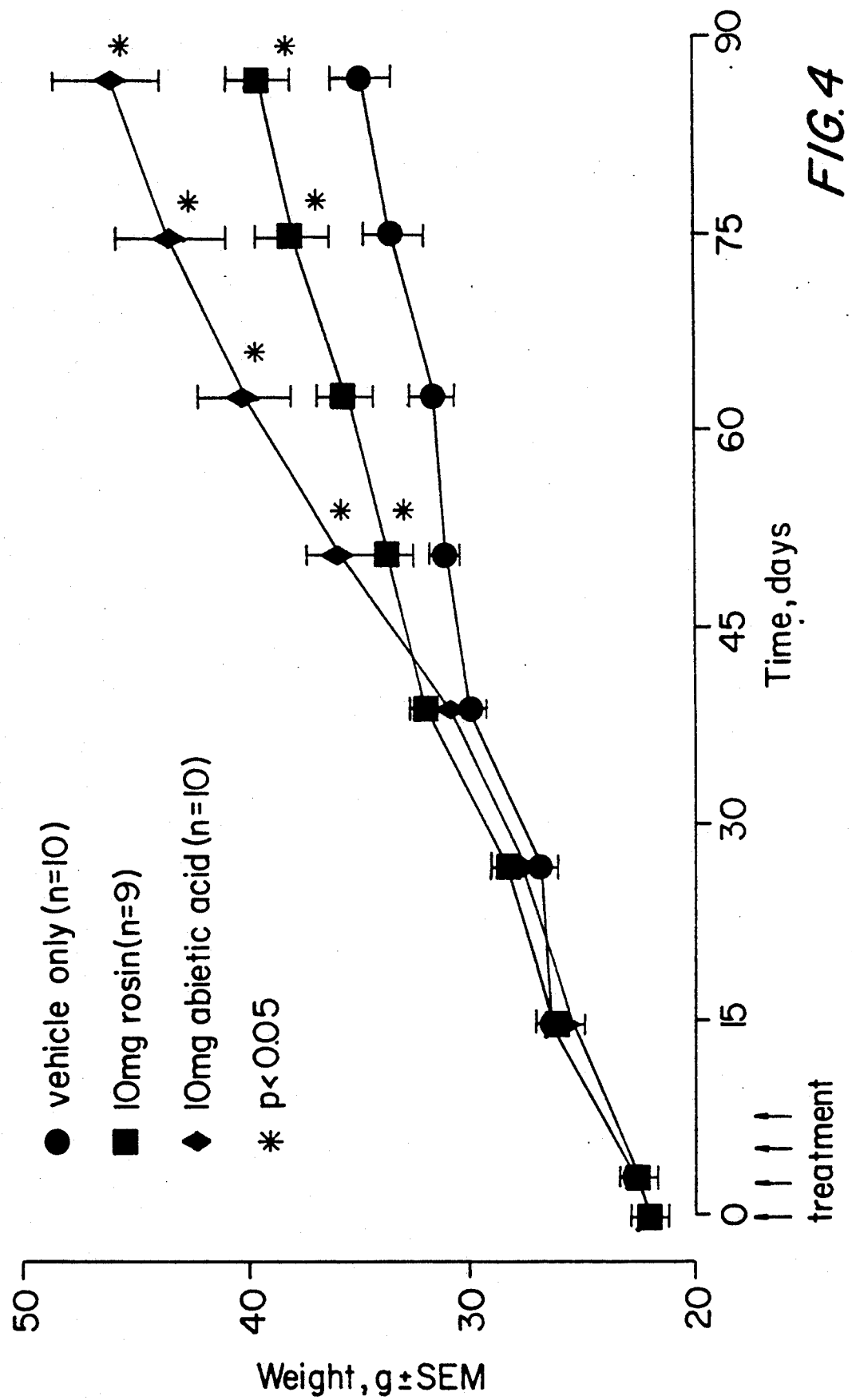
FIG. 4 is a graph comparing weight gain of the mice treated with the compositions of FIG. 3.

FIG. 3 illustrates a significant difference in survival between treated and untreated groups of mice. The only visible side effects were increased weight (FIG. 4) and a slight deterioration of the coat condition, notably in the technical grade abietic acid-treated group. The notation in FIG. 3 on $p<0.05$ establishes that there was statistical significance between the untreated mice and the rosin or technical grade abietic acid treated mice (i.e., the treatment has some effect). It was ascertained upon sacrifice and dissection that the weight increase appeared due to increased deposition of adipose tissue. The asterisks in FIG. 4 denote that the difference between the asterisked group and the control group is statistically significant. These results clearly establish the anti-tumor effect of rosin and technical grade abietic acid.

EXAMPLE 4

Mice were treated in accordance with the procedure described in Example 3 above with the omission of the tumor-laden groups and the groups treated with rosin (i.e., tumor-free mice were treated with either the technical grade abietic acid or vehicle alone). On the twenty-third day after treatment was begun, mice from each group were sacrificed, bled, and the resulting six blood and six serum samples therefrom subjected to respective hematological and chemical analysis. On the twenty-fifth day after the start of treatment, three technical grade abietic acid-treated mice were subjected to necropsy and histological assessment of selected tissues. The survival rate of the treated mice is reported in Table 3, the hematological/chemical analysis is reported in Table 4 and the histological assessment is reported in Table 5 below.

TABLE 3

SURVIVAL OF MICE TREATED INTRAPERITONEALLLY WITH ABIETIC ACID SUSPENSION (4 doses of 430 mg abietic acid/kg) or JUST PBS VEHICLE ALONE (CONTROL)

| Group | Group Size (number of mice) | Survivors at 23 (number of mice) |
| --- | --- | --- |
| Control | 30 | 22* |
| Treated | 30 | 21* |

*$p>0.05$ (chi-squared test)

TABLE 4

BLOOD HEMATOLOGY AND CHEMISTRY OF MICE TREATED INTRAPERITONEALLY WITH ABIETIC ACID SUSPENSION (4 doses of 430 mg/kg) OR JUST VEHICLE ALONE (CONTROL)

| Parameter | Observed Group Mean +/− SEM (n) | | Units | Students |
|---|---|---|---|---|
| | Control | Treated | | |
| Red Blood Cell Count | 8.84 ± 0.16(6) | 8.57 ± 0.26(6) | $10^6$/ul | NS |
| White Blood Cell Count | 3.53 ± 0.25(6) | 3.50 ± 0.39(6) | $10^3$/ul | NS |
| Hematocrit | 48.0 ± 0.86(6) | 45.4 ± 1.48(6) | % | NS |
| Hemoglobin (HB) | 14.6 ± 0.24(6) | 13.9 ± 0.37(6) | g/100 ml | NS |
| Mean Cell Volume | 54.3 ± 0.87(6) | 53.1 ± 1.99(6) | fl | NS |
| Mean Cell Hemoglobin | 16.5 ± 0.16(6) | 16.3 ± 0.27(6) | pg | NS |
| Mean Corpuscular HB Conc. | 30.4 ± 0.54(6) | 30.8 ± 0.98(6) | g/100 ml | NS |
| Segmented Neutrophils | 7.16 ± 0.98(6) | 5.33 ± 1.45(6) | % | NS |
| Band Neutrophils | 0(6) | 0(6) | % | NS |
| Lymphocytes | 91.8 ± 0.95(6) | 93.3 ± 1.69(6) | % | NS |
| Monocytes | 1.0 ± 0.63(6) | 1.3 ± 0.49(6) | % | NS |
| Eosinophils | 0(6) | 0(6) | % | NS |
| Basophils | 0(6) | 0(6) | % | NS |
| Nucleated RBC | 0(6) | 0(6) | /100 WBC | NS |
| Platelets | Adequate (6/6) | Adequate (6/6) | | |
| RBC Morphology | Normal (6/6) | Normal (6/6) | | |
| Glucose | 162 ± 5.8(5) | 152 ± 6.7(6) | mg/100 ml | NS |
| BUN | 14.6 ± 0.51(5) | 16.0 ± 0.89(6) | mg/100 ml | NS |
| Creatinine | 0.40 ± 0.03(6) | 0.38 ± 0.02(6) | mg/100 ml | NS |
| Total protein | 5.54 ± 0.10(5) | 5.43 ± 0.10(6) | g/100 ml | NS |
| Albumin | 3.84 ± 0.04(5) | 3.61 ± 0.11(6) | g/100 ml | $p<0.05$* |
| Calcium | 7.32 ± 0.21(5) | 7.90 ± 0.36(6) | mg/100 ml | NS |
| Inorganic Phosphorus | 8.24 ± 0.17(5) | 9.83 ± 0.41(6) | mg/100 ml | $p<0.05$ |
| Alkaline Phosphatase | 121 ± 11.7(5) | 149 ± 14.6(6) | U/l | NS |
| AST (SGOT) | 303 ± 29.7(5) | 341 ± 44.9(5) | U/l | NS |
| ALT (SGPT) | 74.0 ± 6.9(5) | 66.8 ± 3.9(5) | U/l | NS |
| LDH | 1329 ± 129(5) | 1496 ± 127(5) | U/l | NS |
| Cholesterol | 110 ± 5.2(5) | 119 ± 6.0(5) | mg/100 ml | NS |
| Total Bilirubin | 0.36 ± 0.019(5) | 0.38 ± 0.017(5) | mg/100 ml | NS |
| Amylase | 4988 ± 366(5) | 5704 ± 170(5) | U/l | NS |
| Sodium | 138.0 ± 1.3(5) | 141.3 ± 0.99(6) | meq/l | NS |
| Chloride | 87.4 ± 2.36(5) | 88.0 ± 0.97(6) | meq/l | NS |
| Globulin | 1.70 ± 0.11(5) | 1.82 ± 0.031(6) | g/100 ml | NS |
| Albumin/Globulin Ratio | 2.30 ± 0.154(5) | 2.00 ± 0.078(6) | | NS |
| BUN/Creatinine Ratio | 374 ± 33.0(5) | ·421 ± 26.9(6) | | NS |

*Mann - Whitney ranking test (corrected for ties).

TABLE 5

HISTOLOGICAL ASSESSMENT OF MICE TREATED INTRAPERITONEALLY WITH 4 DOSES OF 430 MG/KG OF ABIETIC ACID SUSPENSION

| Mouse No: | 1 | 2 | 3 |
|---|---|---|---|
| Gross necropsy | | | |
| Heart | — | — | — |
| Lung | — | E | — |
| Liver | A | — | — |
| Spleen | B | B | B |
| Kidney | — | — | — |
| Eyes | — | — | — |
| Other | CD | — | F |
| Histological assessment | | | |
| Heart | — | — | — |
| Liver | G | J | — |
| Spleen | H | H | H |
| Kidney | — | — | K |
| Stomach | I | | |
| Lung | | — | |
| Pancreas | | | L |

Legend

TABLE 5-continued

HISTOLOGICAL ASSESSMENT OF MICE TREATED INTRAPERITONEALLY WITH 4 DOSES OF 430 MG/KG OF ABIETIC ACID SUSPENSION

| Mouse No: | 1 | 2 | 3 |
|---|---|---|---|

— = No significant findings.
A = Liver: The liver adjacent to the spleen had a slightly pale firm area.
B = Spleen: The splenic capsule had a mottled opaque blue appearance.
C = Stomach: The serosal surface appeared to have some diverticula, but no diverticula were observed once the stomach was opened.
D = Small intestine: The small intestine was adhered to the peritoneum.
E = Lung: The right cranial lobe had a dark red wedge shaped focus which disappeared once the lung was inflated with formalin.
F = Pancreas: The pancreas appeared to be slightly enlarged.
G = Liver: The hepatic capsule was mildly thickened with fibrous tissue and a modicum of mononuclear cells and neutrophils. Rare small foci of several neutrophils with or without several mononuclear cells were in the parenchyma. A modicum of neutrophils was also surrounding one bile duct.

TABLE 5-continued
HISTOLOGICAL ASSESSMENT OF MICE TREATED INTRAPERITONEALLY WITH 4 DOSES OF 430 MG/KG OF ABIETIC ACID SUSPENSION

| Mouse No: | 1 | 2 | 3 |
|---|---|---|---|

H = Spleen: The splenic capsule was mildly thickened with fibrous tissue and moderate numbers of mononuclear cells and neutrophils and less amounts of eosinophils. Neutrophils and eosinophils were also present in the parenchyma beneath the capsule. There was also mild lymphoid hyperplasia.
I = Stomach: There was a relatively small focus of fibrous tissue and rare eosinophils on the serosa of the stomach. Several foci of fibrous tissue with mononuclear cells, neutrophils and eosinophils were in the abdominal fat in close proximity to the stomach. A modicum of neutrophils was also in a neighboring abdominal lymph node.
J = Liver: There were rare small foci of several mononuclear cells and a few neutrophils in the parenchyma.
K = Kidney: Cortical cyst.
L = Pancreas: There was a modest amount of fibrous tissue with a few mononuclear cells and neutrophils adjacent to the pancreas.
Final Diagnosis
1. Mild multifocal chronic-active perisplenitis. (Mice Nos. 1, 2 & 3)
2. Mild multifocal chronic-active perihepatitis. (Mouse No. 1)
3. Minimal to mild multifocal chronic-active peritonitis. (Mice Nos. 1 & 2).

Toxicity

There was no conclusive evidence of toxicity but the perisplenitis, perihepatitis and peritonitis were likely secondary to irritation from the test compound. In addition, the presence of the eosinophils in the lesions might be indicative of a possible hypersensitivity (allergic) response.

The data in Table 3 indicate no detectable difference in frequency of unexpected deaths between the two groups of mice while the Table 4 data show no detectable difference between these two groups of mice except for a minor reduction in albumin and a minor increment in inorganic phosphorous in the abietic acid treated mice. In particular, white blood cell count and platelet assessment remained unchanged by treatment with abietic acid. The data in Table 5 shows that there was no conclusive histological evidence of toxicity. The observed perisplenitis, perihepatitis and peritonitis were probably due to secondary irritation from the injected substances.

Table 3 indicates that the intraperitoneal administration of vehicle alone also resulted in a mortality rate of approximately 27%. Most of the deaths for both technical grade abietic acid-treated mice and just the vehicle-treated mice occurred after the fourth injection. This mortality rate is therefore possibly due to the alcoholic content of the vehicle itself. Nevertheless, there is clearly no demonstrable difference in the mortality rate between the control and treated groups of mice establishing that the dose of 430 mg/kg of technical grade abietic acid (administered four times) exhibits no detectable lethal effect over this documented time period. In contrast, the alkylating resin acid derivatives of Table I of the *Pharmaceutical Chemistry Journal* publication cited above, when administered intraperitoneally in starch paste, exhibited an $LD_{50}$ ranging from 30–500 mg/kg, giving a median value of 250 mg/kg. It is therefore clear that technical grade abietic acid has significantly lower acute intraperitoneal toxicity than the alkylating derivatives of resin acids disclosed in the *Pharmaceutical Chemistry Journal* publication.

Table 4 shows that there is little significant difference between the technical grade abietic acid-treated group and the control group with respect to blood hematology and chemistry. There is no demonstrable effect on white blood cell count or platelet status, even after four doses which each exceeded the $LD_{50}$ of alkylating agents derived from resin acids as disclosed in the *Pharmaceutical Chemistry Journal* publication. Alkylating agents as a class of anti-tumor compounds are known to affect rapidly proliferating normal tissue resulting in lowered white blood cells and platelet counts. The white cell count nadir for most alkylating agents is between 7 and 21 days and is often used as the defining limit of clinical treatment (Cline and Haskell, "Drugs Used in Cancer Chemotherapy" Third edition, W. B. Saunders Co. (1980), pages 31–44).

Table 5 shows that histological evaluation of three animals treated with technical grade abietic acid revealed no evidence of toxicity but only minor secondary irritations. Therefore, technical grade abietic acid has significantly lower toxicity than alkylating agents from resin in acids as disclosed in *The Pharmaceutical Chemistry Journal* publication when administered intraperitoneally.

What is claimed is:

1. A method for treating a tumor sensitive to treatment with the compound of the formula below, comprising administering to an individual in need thereof, a tumor-treating effective amount of at least one compound of the formula:

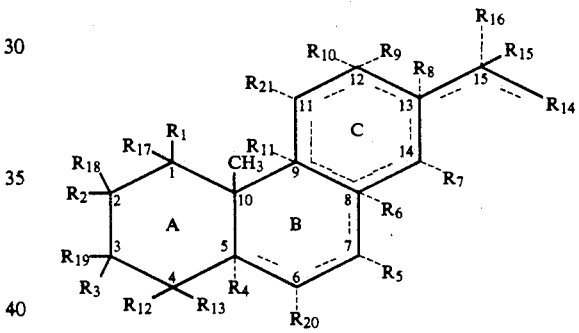

where $R_1=H$; $R_2=H$; $R_3=H$; $R_4=H$; $R_5$ when present$=H$; $R_6$ when present$=H$; $R_7$ when present$=H$; $R_8$ when present$=H$ or $CH_3$; $R_9$ when present$=H$; $R_{10}$ when present$=H$; $R_{11}$ when present$=H$; $R_{12}=CH_3$; $R_{13}$ is $CH_3$ or COOH; $R_{14}$ is H, $CH_2$ or $CH_3$; $R_{15}=H$ or $CH_3$; $R_{16}$ when present$=H$ or $CH_3$; $R_{17}=H$; $R_{18}=H$; $R_{19}=H$; $R_{20}$ when present$=H$; and $R_{21}$ when present$=H$, or the pharmaceutically acceptable salts thereof.

2. The method of claim 1, wherein said compound is at least one member selected from the group consisting of 18-abietanoic acid; 13 beta-abietan-18-oic acid; 8 alpha, 13 beta-abieten-18-oic acid; 9 beta, 13 beta-abietan-18-oic acid; 7-abieten-18-oic acid; 13 beta-abiet-7-en-18-oic acid; 8-abieten-18-oic acid; 13 beta-abiet-8en-18-oic acid; 8(14)-abieten-18-oic acid; 13 beta-abiet-8(14)-en-18-oic acid; 13-abieten-18-oic acid; 8 alpha-abiet-13-en-18-oic acid; 13(15)-abieten-18-oic acid; 7, 13-abietadien-18-oic acid; 8, 13-abietadien-18-oic acid; 8, 12-abietadien-18-oic acid; 8,13(15)-abietadien-18-oic acid; 8(14), 13(15)-abietadien-18-oic acid; 13 beta-abieta-7,9(11)-dien-18-oic acid; 8(14), 12-abietadien-18-oic acid; 8,11,13-abietatrien-18-oic acid; 6,8,11,13-abietatetraen-18-oic acid; 5 beta-abieta-8,11,13-trien-18-oic acid; 18-isopimaranoic acid; 8 alpha-isopimaran-18-oic acid; 7-isopimaren-18-oic acid; 8-isopimaren-18-oic acid;

8(14)-isopimaren-18-oic acid; 7,15-isopimaradien-18-oic acid; 8,15-isopimaradien-18-oic acid; 8(14),15-isopimaradien-18-oic acid; 18-pimaranoic acid; 8 alpha-pimaran-18-oic acid; 8-pimaren-18-oic acid; 8(14)-pimaren-18-oic acid; 8,15-pimaradien-18-oic acid; and 8(14),15-pimaradien-18-oic acid.

3. The method of claim 2, wherein $R_6$ is not present, there being unsaturation present at the no. 8 position on the fused ring structure between rings B and C, $R_{13}$=COOH, and $R_{14}$=CH$_2$ or CH$_3$.

4. The method of claim 3, wherein said compound is at least one member selected from the group consisting of 8,15-isopimaradien-18-oic acid; 8,15-pimaradien-18-oic acid; 7,15-isopimaradien-18-oic acid; 13 beta-abieta 7,9(11)-dien-18-oic acid; 5 beta-abieta-8,11,13-trien-18-oic acid; 8,12-abietadien-18-oic acid; 7,13-abietadien-18-oic acid, and 8(14), 13(15)-abietadien-18-oic acid.

5. The method of claim 4, wherein said compound is 7,13-abietadien-18-oic acid.

6. The method of claim 1, wherein the compound is administered at a daily dosage of about 100 to about 800 mg/kg individual.

7. The method of claim 6, wherein the compound is administered at a daily dosage of about 200 to about 700 mg/kg individual.

8. The method of claim 7, wherein the compound is administered at a daily dosage of about 300 to about 600 mg/kg individual.

9. The method of claim 1, wherein the compound is effective against tumors selected from the group consisting of non-small cell lung cancer, small cell lung cancer, colon cancer, CNS cancer, melanoma, ovarian cancer and renal cancer.

10. The method of claim 1, wherein said compound is effective against tumors selected from the group, consisting of L929 cells, S180 cells, and Ehrlich-Lettre Carcinoma cells.

* * * * *